US00PP36869P2

(12) United States Plant Patent
Li

(10) Patent No.: US PP36,869 P2
(45) Date of Patent: Jul. 29, 2025

(54) ***SPATHIPHYLLUM* PLANT NAMED 'QUEENIE'**

(50) Latin Name: *Spathiphyllum wallisii regel*
Varietal Denomination: QUEENIE

(71) Applicant: Zhongshan Brighten Floriculture Ltd., Zhongshan (CN)

(72) Inventor: Peifeng Li, Zhongshan (CN)

(73) Assignee: Zhongshan Brighten Floriculture LTD

( * ) Notice: Subject to any disclaimer, the term of this patent is extended or adjusted under 35 U.S.C. 154(b) by 0 days.

(21) Appl. No.: 18/787,416

(22) Filed: Jul. 29, 2024

(51) Int. Cl.
*A01H 5/12* (2018.01)
*A01H 6/10* (2018.01)

(52) U.S. Cl.
USPC ..... Plt./364

(58) Field of Classification Search
USPC ..... Plt./373, 364
See application file for complete search history.

*Primary Examiner* — Susan McCormick Ewoldt

(57) ABSTRACT

A new and distinct cultivar of *Spathiphyllum* plant named 'QUEENIE' is disclosed, characterized by shiny dark green foliage, moderately wavy leaves, abundant flowers, and robust flower stalks. The new variety is a *Spathiphyllum*, typically produced as an indoor ornamental plant.

1 Drawing Sheet

Latin name of the genus and species: *Spathiphyllum wallisii regel.*
Variety denomination: 'QUEENIE'.

BACKGROUND OF THE INVENTION

The new cultivar is a product of a planned breeding program by the inventor. The new variety originated from a crossing of the seed parent, the unpatented *Spathiphyllum* 'Cody's Color', and the pollen parent, the unpatented *Spathiphyllum* 'Sweet Romano'. The crossing was made at a greenhouse facility in Zhongshan, Guangdong, China in 2011.

The new variety was discovered by the inventor in 2012 in a group of seedlings resulting from the crossing, at the same location in Zhongshan, Guangdong, China.

Asexual reproduction of the new cultivar 'QUEENIE' was first performed by tissue culture in a commercial tissue culture laboratory in Binyun, China in November 2013. Subsequent propagation has shown that the unique features of this cultivar are stable and reproduced true to type.

SUMMARY OF THE INVENTION

The cultivar 'QUEENIE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'QUEENIE.' These characteristics in combination distinguish 'QUEENIE' as a new and distinct *Spathiphyllum* cultivar:

1. Dark green foliage.
2. Moderately wavy leaves.
3. Abundant spathe production, robust flower stalks, and strong clumping.
4. Thick and shiny leaves.

PARENT COMPARISONS

'QUEENIE' can be compared to the seed parent in most horticultural characteristics, however, 'QUEENIE' differs in the following:

1. Foliage color of the new variety is a deeper green than the foliage color of the seed parent.
2. Flower clusters of the new variety are larger than the flower clusters of the seed parent.
3. Foliage of the new variety is glossier than the foliage of the seed parent.

'QUEENIE' can be compared to the pollen parent in most horticultural characteristics, however, 'QUEENIE' differs in the following:

1. Plants of the new variety are smaller in stature than plants of the pollen parent.
2. Plants of the new variety have shiny and distinctly wavy leaves, while plants of the pollen parent have very weakly wavy leaves.
3. Leaves of the new variety are smaller than leaves of the pollen parent.

COMMERCIAL COMPARISONS

'QUEENIE' can be compared to the commercial variety *Spathiphyllum* 'Mojo', unpatented. Plants of 'Mojo' are similar to plants of 'QUEENIE' in most horticultural characteristics, however, 'QUEENIE' differs in the following:

1. Foliage color of the new variety is a darker green than the foliage color of this comparator.
2. Clumping of the new variety is stronger than branching of this comparator.
3. Plants of the new variety have shiny and distinctly wavy leaves, while plants of this comparator have no, or very weakly wavy leaves.

'QUEENIE' can be compared to the commercial variety *Spathiphyllum* 'Gorgusis No. 1' U.S. Plant Pat. No. 6,964. Plants of 'Gorgusis No. 1' are similar to plants of 'QUEENIE' in most horticultural characteristics, however, 'QUEENIE' differs in the following:

1. Plants of the new variety are smaller in stature than plants of this comparator.
2. Plants of the new variety produce more spathes than plants of 'Gorgusis No. 1'.

BRIEF DESCRIPTION OF THE PHOTOGRAPH

The accompanying photograph illustrates in full color a typical plant of 'QUEENIE' grown in a greenhouse in Zhongshan, Guangdong, China. This plant is approximately 10 months old, shown in an 11 cm pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'QUEENIE' plants grown in a greenhouse in Zhongshan, Guangdong, China. Temperatures ranged from 10° C. to 30° C. at night to 10° C. to 40° C. during the day. No artificial light, photoperiodic treatments were given to the plants. Plants were treated with Gibberellic Acid at 200-400ppm, to induce flowering. Plants were grown in the shade. Measurements and numerical values represent averages of typical plant types.

Botanical classification: *Spathiphyllum wallisii regel* 'QUEENIE'.

PROPAGATION

Time to initiate roots: Approximately 21 days at approximately 25° C. to 27° C.

Time to produce a fully rooted plantlet: Approximately 8 weeks at approximately 25° C. to 27° C.

Root description: Freely branching, numerous fleshly roots with finer lateral roots.

PLANT

Growth habit: Strong clumping from base, bushy and dense.

Plant shape: Broad inverted triangle with flowers above leaf plane.

Height: Approximately 28 cm to top of highest leaf; approximately 52 cm to top of highest spathe.

Plant spread: Approximately 45 cm in a 11 cm pot.

Container size: 9 to 11 cm.

Growth rate: Moderate. It takes approximately one year to fully grow. On average, it grows about 3-4 cm per month, with a slower growth rate in the first few months.

Branching characteristics: No branching. Leaves emerge direct from base of plant.

Number of clumps of leaves: Average 12.

Number of leaves per clump: Average 7.

Number of leaves per plant: Approximately 84.

Age of plant described: Approximately 10 months.

FOLIAGE

Leaf:

- *Arrangement.*—Alternate, growing directly from the soil.
- *Average Length (excluding petiole).*—Approximately 17.7 cm.
- *Average Width.*—Approximately 6.3 cm.
- *Shape of blade.*—Orbicular-ovate.
- *Aspect.*—Slightly carinate, slightly curved, pointed outward-upright.
- *Apex.*—Long tail tip.
- *Base.*—Attenuate.
- *Margin.*—Moderately undulate.
- *Texture of top surface.*—Highly glossy.
- *Texture of bottom surface.*—Smooth, moderately glossy.
- *Color.*—Young foliage upper side: Near RHS Green 137A. Young foliage under side: Near RHS Green 137B. Mature foliage upper side: Near RHS Green 139A. Mature foliage under side: Near RHS Green 137A.

Venation:

- *Type.*—Pinnate.
- *Color, upper side.*—Near RHS Green N137B.
- *Color, under side.*—Near RHS Yellow-Green 143C.

Petiole (excluding geniculum):

- *Length.*—Approximately 19 cm.
- *Width.*—At geniculum: Approximately 0.4 cm. Above clump: Approximately 0.6 cm.
- *Color.*—Near RHS Green 138B.
- *Strength.*—Moderately strong.

Geniculum:

- *Length.*—Approximately 2.5 cm.
- *Width.*—Approximately 0.3 cm.
- *Color.*—Near RHS Green 137B.

INFLORESCENCE

Arrangement: The spathe terminates in a straight peduncle that opens vertically above the leaves.

Flowering habit: Continuous.

Quantity of spathes per plant: On average 5-10 fully open spathes in good condition.

Natural flowering season: Winter to spring.

Time to flowering: Approximately 40 weeks from a rooted young plant.

Fragrance: Moderately strong, sweet and pleasant.

Self-cleaning or persistent: Persistent.

Flower longevity: Flowers stay in good condition approximately 3 weeks on the plant.

Spathe:

- *Aspect.*—Upright.
- *Length.*—Approximately 14.2 cm.
- *Width.*—Approximately 6.7 cm.
- *Shape.*—Ovate, concave.
- *Margin.*—Entire.
- *Apex.*—Apiculate.
- *Base.*—Attenuate.
- *Color.*—Front when opening: Near RHS White 157C. Back when opening: Near RHS White 155C. Front when mature: Near RHS White 155C. Back when mature: Near RHS White 155C. Fading to: Not fading.

Spadix:

- *Shape.*—Columnar, arising from top of peduncle.
- *Tip.*—Obtuse.
- *Base.*—Obtuse.
- *Length.*—Approximately 4.7 cm.
- *Width.*—Approximately 1.7 cm.
- *Color.*—When opening: Near RHS White NN155A. Mature: Near RHS White 155D.
- *Quantity of flowers per spadix.*—Approximately 95.
- *Spadix flower arrangement.*—Spirally placed on spadix.
- *Spadix flower diameter.*—Approximately 0.2 cm.
- *Spadix flower depth.*—Approximately 0.3 cm.

Peduncle:

*Length.*—Approximately 38 cm.

*Width.*—Approximately 0.5 cm.

*Color.*—Near RHS Green 137C.

*Strength.*—Moderately strong.

REPRODUCTIVE ORGANS

General description of visible parts: Three stigmas are placed on top of each ovary (length of ovary approximately 0.35 cm), stigma diameter approximately 0.1 cm, colored near RHS White N155D.

OTHER CHARACTERISTICS

Disease resistance: Neither resistance nor susceptibility to typical diseases and pests of *Spathiphyllum* have been observed.

Drought tolerance and cold tolerance: The new cultivar is a typical *Spathiphyllum*, an indoor plant with no frost tolerance.

Fruit/seed production: Not observed.

What is claimed is:

1. A new and distinct cultivar of *Spathiphyllum* plant named 'QUEENIE' as herein illustrated and described.

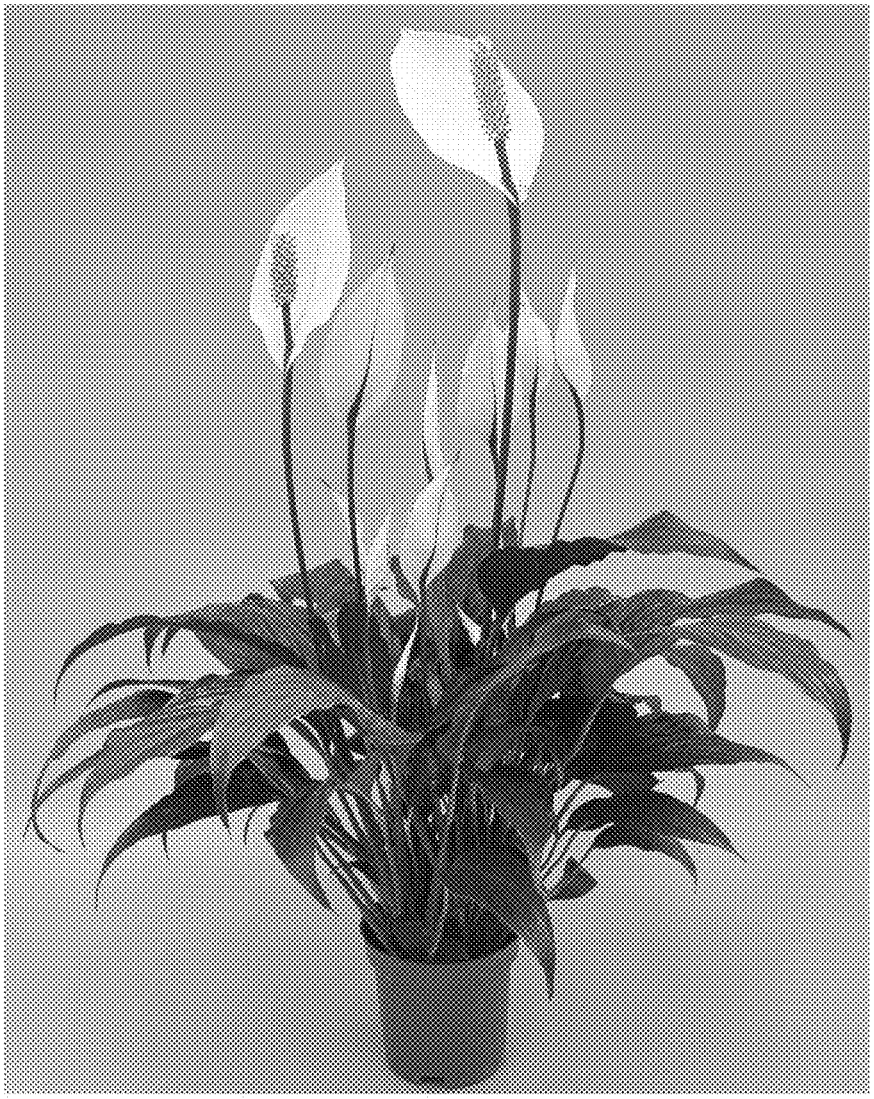

* * * * *